United States Patent [19]

Vladuchick

[11] 4,110,335
[45] Aug. 29, 1978

[54] PROCESS FOR PREPARING DISALTS OF 3,4-DIMERCAPTOISOTHIAZOLE-5-CARBONITRILE [AND RELATED PRODUCTS THEREFROM]

[75] Inventor: Susan Anne Vladuchick, Newark, Del.

[73] Assignee: E. I. Du Pont de Nemours and Company, Wilmington, Del.

[21] Appl. No.: 790,856

[22] Filed: Apr. 25, 1977

Related U.S. Application Data

[62] Division of Ser. No. 704,973, Jul. 13, 1976, Pat. No. 4,066,656.

[51] Int. Cl.$^2$ .............................................. C07D 275/02
[52] U.S. Cl. .................................................. 260/302 S
[58] Field of Search .................................... 260/302 S

*Primary Examiner*—Donald G. Daus
*Assistant Examiner*—D. B. Springer

[57] ABSTRACT

Described is a process for preparing 3,4-dimercaptoisothiazole-5-carbonitrile disalt, preferably disodium salt, and its conversion to 1,4-dithiino[2,3-c; 6,5-c']-diisothiazole-3,7-dicarbonitrile through an intermediate dimeric structure believed to be [1,2,5,6]tetrathiocino-[3,4-c; 7,8-c']diisothiazole-3,8-dicarbonitrile. 3,4-Dimercaptoisothiazole-5-carbonitrile disodium salt and [1,2,5,6]tetrathiocino[3,4-c; 7,8-c']diisothiazole-3,8-dicarbonitrile are useful rubber curing agents, and 1,4-dithiino[2,3-c; 6,5-c']diisothiazole-3,7-dicarbonitrile is the immediate precursor of 1,4-dithiino[2,3-c; 6,5-c']diisothiazole-3,7-dicarboxylic acid, a yellow pigment.

8 Claims, No Drawings

PROCESS FOR PREPARING DISALTS OF 3,4-DIMERCAPTOISOTHIAZOLE-5-CARBONITRILE [AND RELATED PRODUCTS THEREFROM]

BACKGROUND OF THE INVENTION

Field of the Invention

This invention relates to processes for preparing disalts of dimercaptoisothiazoles, processes for preparing dimers and diisothiazoles from the disalts, and novel isothiazole dimers.

Prior Art

1. U.S. Pat. No. 3,197,472 issued July 27, 1965 to R.D. Vest describes a salt of 3,4-dimercaptoisothiazole-5-carbonitrile as the co-product of the reaction of p-dithiino [c]-isothiazole-3,5,6-tricarbonitrile with potassium dimethyldithiocarbamate. This co-product was not further identified or characterized.

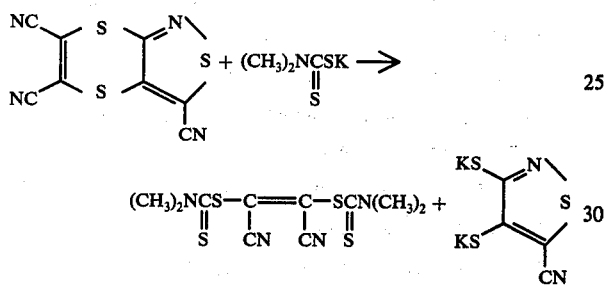

2. Coassigned application Ser. No. 625,132, filed Oct. 23, 1975, discloses alternative processes for preparing 1,4-dithiino[2,3-c; 6,5-c']diisothiazole-3,7-dicarbonitrile, and claims this compound, the corresponding dicarboxylic acid and the parent heterocycle as compositions of matter. 3. U.S. Pat Nos. 3,149,107 (Sept. 15, 1964), 3,230,229 (Jan. 18, 1966) and 3,232,935 (Feb. 1, 1966) all issued to W. R. Hatchard, and W. R. Hatchard, J. Org. Chem., 28, 2163 (1963), 29, 660, 665 (1964) disclose that the reaction of dimercaptomethylenemalonitrile disodium salt (a structural isomer of Bähr's salt) with sulfur in hot methanol gives 3,5-dimercaptoisothiazole-4-carbonitrile disodium salt (a structural isomer of 3,4-dimercaptoisothiazole-5-carbonitrile disodium salt).

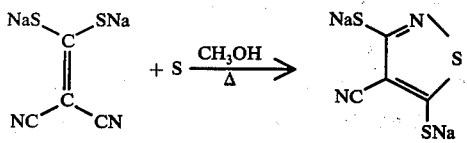

Because of its structure, the described isomer cannot dimerize in the same way as the compound described herein, and consequently it is not convertible to 1,4-dithiino[2,3-c; 6,5-c']diisothiazole-3,7-dicarbonitrile. 3,5-Dimercaptoisothiazole-4-carbonitrile and its derivatives are also described by E. Söderbäck, Acta Chem. Scand., 17, 362 (1963), G.A. Hoyer and M. Kless, Tetrahedron Letters, 4265 (1969) and British Pat. No. 1,124,545 (Aug. 21, 1968 to E. Merck).

SUMMARY OF THE INVENTION

According to the present invention there is provided a process for preparing a disalt, preferably the disodium salt, of 3,4-dimercaptoisothiazole-5-carbonitrile comprising contacting a 1,2-dimercaptomaleonitrile salt of the formula

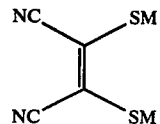

where M is an alkali metal or bis [tetra (lower alkyl) ammonium)], with sulfur in an alcohol solvent at a temperature of at least 50° C.

There is also provided a process wherein the disalt is contacted with an oxidizing agent to form [1,2,5,6]tetrathiocino[3,4-c; 7,8-c']diisothiazole-3,8-dicarbonitrile, or its position isomer, which can then be heated with or without a catalyst to form 1,4-dithiino[2,3-c; 6,5-c']diisothiazole 3,7-dicarbonitrile.

The disodium salt of 3,4-dimercaptoisothiazole-5-carbonitrile and [1,2,5,6]tetrathiocino[3,4-c; 7,8-c']diisothiazole-3,8-dicarbonitrile are useful rubber curing agents. 1,4-dithiino[2,3-c; 6,5-c']diisothiazole-3,7-dicarbonitrile and its conversion to the corresponding -3,7-dicarboxylic acid or other derivatives is described in the aforesaid application Serial No. 625,132.

DETAILED DESCRIPTION OF THE INVENTION

The reaction between carbon disulfide and sodium cyanide to form 1,2-dimercaptomaleonitrile disodium salt (1) (Bähr's salt) is described by G. Bähr and G. Schleitzer, Chem. Ber., 88, 1771 (1955), 90, 438 (1957) and provides the starting material for this invention

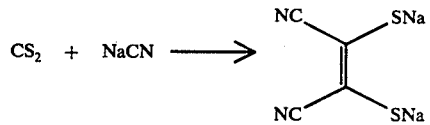

1

The trans-isomer of 1, 1,2-dimercaptofumaronitrile disodium salt (2), was prepared by H. E. Simmons, D. C. Blomstrom and R. D. Vest, J. Amer. Chem. Soc., 84, 4756 (1962) by oxidation of 1 to a cis-cis-disulfide which can be converted to 2 by isomerization and reduction.

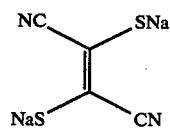

2

One aspect of the present invention is illustrated by the following reaction where 1 is reacted with sulfur to make 3,4-dimercaptoisothiazole-5-carbonitrile disodium salt 3.

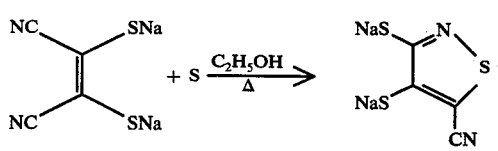

Depending upon the reaction conditions, 3 may be accompanied by 2. In the preferred process, a catalyst is used which converts 1 cleanly to 3; unreacted 1 and its isomer 2 are not present in the product.

When the reactants are heated together in an alcohol solvent without a catalyst, the conversion of 1 to 3 occurs very slowly and incompletely and is accompanied by the formation of 2 as shown in Example 1. The addition of a catalyst such as tetracyano-1,4-dithiin (4) (Examples 2-7), 3-[(2-mercapto-1,2-dicyanovinyl)mercapto]-4-mercaptoisothiazole-5-carbonitrile bis[tetra (lower alkylammonium)] salt such as the tetrapropylammonium salt shown in (5) (Example 8), or the use of mother liquors of

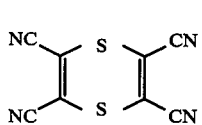

4

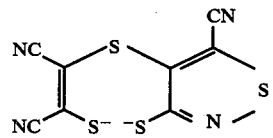

(Pr$_4$N$^+$)$_2$

5 previous reactions which contain the dianion of 5 reduces reaction time to a few hours and gives an easily separable product 3. Alternatively, the reaction mixture can contain an oxidizing agent which is not reactive with the solvent and which generates 4 from 1. H. E. Simmons, R. D. Vest, D. C. Blomstrom, J. R. Roland and T. L. Cairns, *J. Amer. Chem. Soc.*, 84, 4746 (1962) list several such oxidizing agents; the following oxidizing agents are compatible with the alcohol solent used in the process of this invention: chlorine, bromine, iodine, potassium hexacyanoferrate (III) and ammonium persulfate. The catalyzed reaction takes from two to twelve hours for completion with two to four hours usually being sufficient.

In the process for the conversion of 1 to 3, no set order of addition of reagents is necessary. The stoichiometry of the reaction requires one gram-atom of sulfur per mole of 1. However, the reaction will occur over a wide range of molar ratios of these two reagents; but it is preferred to use about 1.0-1.2 g-atoms of sulfur per mole of 1 and about 0.1 mole of catalyst. A large excess of sulfur requires the removal of unreacted sulfur by filtration at the end of the reaction; and less than the required amount of sulfur will contaminate the product 3 with difficulty removable 1.

The reaction proceeds in alcohol solvents, preferably alkanols of 1-6 carbon atoms such as methanol (bp 64.7° C), ethanol (bp 78.5° C), 1-propanol (bp 97.4° C), 1-butanol (bp 117.4° C), 2-hexanol (bp 137°-38° C) and mixtures of these with water and dipolar aprotic solvents such as 1,2-dimethoxyethane, N,N-dimethylformamide, tetrahydrofuran, N,N-dimethylacetamide and dioxane. Pure polar nonalcoholic solvents such as 1,2-dimethoxyethane cannot be used because they cause isomerization of 1 to 2 and effectively stop the reaction at this point. The preferred solvent is ethanol. The amount of solvent used can be from 8 to 40 times the weight (10 to 50 volumes) of 1,2-dimercaptomaleonitrile disodium salt, with 10 to 12 times the weight (12 to 15 volumes) being preferred.

The temperature of the reaction is elevated, e.g., over 50° C and is preferably from about 50°-150° C, and is most preferably from about 50°-100° C. It is convenient to allow the reaction to proceed at the reflux temperature of the solvent, which for the above preferred C$_1$ to C$_6$ alcohols lies in the range of about 60° C-140° C at atmospheric pressure.

The reaction can be carried out at pressures of one to 100 atm, and is preferably done at 1 atm in a vessel equipped with a stirrer, reflux condenser and source of heat. It is preferable to blanket the reaction with nitrogen to minimize oxidative side reactions.

Other salts of 1,2-dimercaptomaleonitrile can be used in place of the disodium salt 1 as starting materials. These other salts are prepared from the disodium salt, e.g., by the procedure described by H. E. Simmons, D. C. Blomstrom and R. D. Vest, *J. Amer. Chem. Soc.* 84, 4756 (1962) for the preparation of the bis(tetramethylammonium)salt, or by ionexchange on a column of a suitable resin. The alkali metal salts such as dilithium, dipotassium, dirubidium, dicesium, and other bis[tetra (lower alkylammonium)] salts such as bis(tetraethylammonium), bis(tetrapropylammonium) and bis(tetrbutylammonium) can be substituted for 1 in the preparation of 3. The disodium salt 1 is the preferred starting material because of its ease of preparation and handling.

3,4-Dimercaptoisothiazole-5-carbonitrile disodium salt is a useful curing agent for natural rubber. It is also oxidized to [1,2,5,6]-tetrathiocino[3,4-c; 7,8-c']diisothiazole-3,8-dicarbonitrile (6) which in turn can be heated to prepare 1,4-dithiino[2,3-c; 6,5-c']diisothiazole-3,7-dicarbonitrile (7) according to the following reactions:

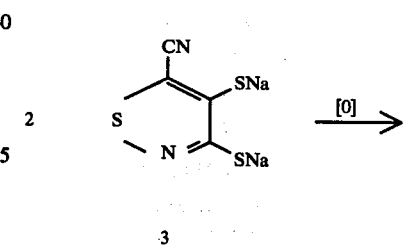

-continued

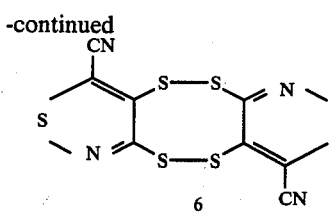

6

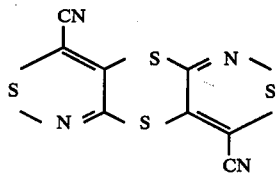

7

The oxidation of 3 to 6 can be carried out with oxidizing reagents commonly used to convert mercaptans or their salts to disulfides, e.g., bromine, hydrogen peroxide such as acidified hydrogen peroxide, iodine, sodium hypochlorite, sodium hypobromite, iron (III) chloride and potassium hexacyanoferrate (III), as described in "Preparative Organic Chemistry," G. Hilgetag and A. Martini, editors, John Wiley, New York, 1972, p. 665–666. The choice of oxidant is governed by the observation that stronger oxidizing agents than those cited will convert mercaptans and disulfides to sulfonic acids and other products. Bromine and acidified hydrogen peroxide are the preferred reagents for this oxidation; bromine gives better yields, but acidified hydrogen peroxide gives a purer product and is the oxidant of choice.

The conversion of 3 to 6 is carried out with bromine by adding excess bromine to a stirred suspension of 3 in an organic solvent such as acetonitrile, dichloromethane, or chloroform. The stoichiometry of the reaction requires one mole of bromine per mole of 3; amounts of up to 5 moles of bromine per mole of 3 can be employed; preferably about 2 moles of bromine per mole of 3 is sufficient to complete the reaction. The preferred solvent is acetonitrile which should be present in an amount sufficient to permit efficient stirring, e.g., from 5 to 15 times the volume of the other reagents. The reaction occurs at about 0° C to about 25° C, the addition of bromine being preferably done at 0° C, and the reaction being allowed to go to completion by stirring at room temperature. The total reaction time is from 1 to 6 hours, usually about 2 hours, approximately equally divided into periods at 0° C and at 25° C. The resulting insoluble product 6 is then filtered from the solvent.

The oxidation of 3 to 6 with hydrogen peroxide, preferably acidified hydrogen peroxide, is carried out with an aqueous suspension of 3 to which 30% aqueous hydrogen peroxide and dilute sulfuric acid as the acidifying agent are added. These two reagents can be added simultaneously from two separate addition funnels, or they can be added as a premixed aqueous solution. The stoichiometry of this reaction requires one mole of hydrogen peroxide and one mole of sulfuric acid for the oxidation of each mole of 3. The use of a large excess of hydrogen peroxide is not recommended because lowered yields are observed even though product 6 can be readily separated from, and washed free of, excess peroxide on a filter. From one to four moles of hydrogen peroxide and sulfuric acid per mole of 3 can be employed; preferably, 1.0 to 1.2 moles per mole of 3 are used.

Control of pH of the solution during this reaction is important and can be monitored with a pH meter. The oxidation will occur between about pH 5 and 10, preferably at about pH 6 to 7. More alkaline solutions promote the decomposition of prdouct 6; thus, it is advantageous to operate in a slightly acidic medium. The volume of water chosen should be sufficient to permit thorough mixing of the suspended 3 and 6, e.g., from 10 to 50 times the volume of 3, and preferably from 20 to 25 times this volume.

The reaction time can be from 1 to 24 hours, with 1 to 3 hours usually sufficient. Higher yields of products are favored by relatively short reaction times (0.5 to 1 hour) after the peroxide addition is complete.

The reaction temperature can be between about −20° C and +100° C, with about 0° C–5° C preferred. The reaction is preferably done in an open vessel at atmospheric pressure. Examples 11–14 illustrate that better yields are obtained with stoichiometric proportions of reagents, low temperature, slightly acidic conditions, and limited reaction times.

Product 6 has been written as the structure given, but it could be the isomeric [1,2,5,6]tetrathiocino[3,4,-c;7,8-c']diisothiazole-3,6-dicarbonitrile 8.

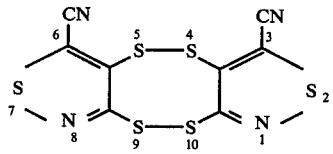

8

Analytical and spectral evidence favors structure 6. Structure 7, the thermolysis product of 6, has been verified by x-ray crystallography.

[1,2,5,6]Tetrathiocino[3,4-c; 7,8-c']diisothiazole-3,8-dicarbonitrile (6) is also a useful curing agent for rubber, and is an intermediate to 1,4-dithiino-[2,3-c; 6,5-c']diisothiazole-3,7-dicarbonitrile (7).

The conversion of 6 to 7 can be carried out by heating 6 in a suitable high boiling organic solvent, preferably in the presence of a catalyst. Solvents which can be used for this reaction have boiling points between 150° C and 300° C, preferably 150°–225° C, are inert, i.e. non-reactive with the di- or tetra-thio compounds, are stable to thermal decomposition, and allow separation of product 7. Examples of such solvents are 1,2,3-trichlorobenzene (bp 218°–219° C), 1,2,4-trichlorobenzene (bp 213.5° C), 1,3,5-trichlorobenzene (bp 208° C), dimethyl sulfoxide (bp 189° C), diphenyl ether (bp 259° C), tetramethylene sulfone (bp 285° C), dimethyl phthalate (bp 282° C), N,N-dimethyl acetamide (bp 165° C), glycol monomethyl ether (bp 190° C), diethylene glycol dimethyl ether (bp 161° C), and N,N-dimethylformamide (bp 153° C). When trichlorobenzene is used as the solvent, the preferred reaction temperature is reflux and the preferred reaction time is overnight to complete the reaction. When N,N-dimethylformamide containing 10 to 25 mol %, preferably 20 to 25 mol %, based on [1,2,5,6]tetrathiocino[3,4-c; 7,8-c']diisothiazole-3,8-dicarbonitrile (6), of disodium salt 3 as catalyst is used, the reaction occurs at lower temperatures, e.g., from about 80° C to 155° C, preferably from 80° C to 100° C.

As described in the aforesaid application Ser. No. 625,132, compound 7 is also obtained by treatment of tetracyano-1,4-dithiin (4) with sulfur. It is a useful intermediate to 1,4-dithiino[2,3-c; 6,5-c']-diisothiazole-3,7-dicarboxylic acid which is a yellow fluorescent dye and pigment; to the dipotassium salt which is an acid-base indicator; to the diacid chloride which forms fluorescent polyamides; and to 1,4-dithiino-[2,3-c; 6,5-c']diisothiazole which is a fluorescence brightener for fabrics.

SPECIFIC EMBODIMENTS OF THE INVENTION

The following illustrative examples demonstrate ways of carrying out the invention. All parts and percentages are by weight, and all temperatures are Centigrade, unless otherwise stated. Characterization data include infrared (IR), ultraviolet (UV), nuclear magnetic resonance (NMR) and mass spectra (MS).

EXAMPLE 1

3,4-Dimercaptoisothiazole-5-carbonitrile Disodium Salt (3) (Preparation Without Catalyst)

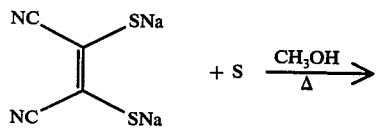

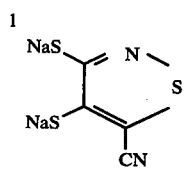 + 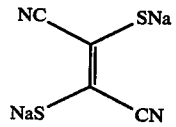

A mixture of 1,2-dimercaptomaleonitrile disodium salt (1) (Bähr's salt, G. Bähr and G. Schleitzer, *Chem. Ber.*, 88, 1771 (1955), 90, 438 (1957)) (18.6 g, 0.10 mol), sulfur (3.2 g, 0.10 g-atom) and methanol (500 ml) was heated at reflux for 41 hours. The mixture was cooled and filtered to remove unreacted sulfur, and the filtrate was evaporated to leave a residue. Infrared analysis showed that this consisted of starting material ($\lambda_{max}$ 4.5 and 11.7 μm), 1,2-dimercaptofumaronitrile disodium salt (2) (trans isomer of Bähr's salt, $\lambda_{max}$ 4.51 and 12.11 μm) and 3,4-dimercaptoisothiazole-5-carbonitrile disodium salt (3) ($\lambda_{max}$ 4.5 and 10.5 μm). These three components were not easily separable. The progress of the conversion of Bähr's salt into the isothiazole derivative can be followed by monitoring the changes in size of the 11.7 and 10.5 μm peaks in the infrared.

EXAMPLE 2

3,4-Dimercaptoisothiazole-5-carbonitrile Disodium Salt (3) (Tetracyano-1,4-dithiin Catalyst)

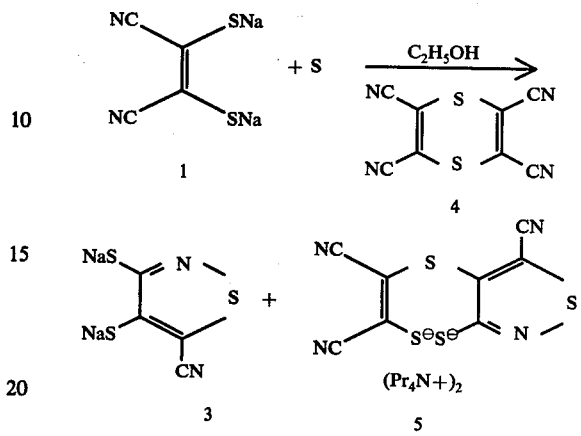

A mixture of 1,2-dimercaptomaleonitrile disodium salt (1) (18.6 g, 0.10 mol), sulfur (4.0 g, 0.125 g-atom), and tetracyano-1,4-dithiin (4) (H. E. Simmons, R. D. Vest, D. C. Blomstrom, J. R. Roland and T. L. Cairns, *J. Amer. Chem. Soc.* 84, 4746 (1962)) (2.16 g, 0.01 mol) and ethanol (250 ml) was heated at reflux for 2 hours. The mixture was filtered hot and cold successively to remove sulfur, and the filtrate was evaporated to leave a yellow residue. This material was extracted with warm (50° C) acetonitrile and filtered under nitrogen; both the residue and the filtrate were saved.

The residue was crude 3,4-dimercaptoisothiazole-5-carbonitrile disodium salt (3) (10.2 g, 0.047 mol, 47% yield) which was characterized by conversion to 4,5-bis-(methylmercapto) isothiazole-5-carbonitrile (9) by stirring a small portion of it with a solution of dimethyl sulfate in acetonitrile at 25° C for a few minutes. The residue obtained

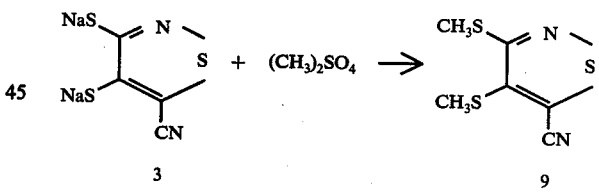

by evaporation of the solvent was chromatographed on acidic alumina using benzene as the solvent. The solid material thus obtained was recrystallized from 1-chlorobutane by cooling the solution to −80° C to give the colorless bis(methylmercapto) derivative 9, mp 63.5°–64° C. This product was also obtained by treating the disodium salt 3 (9.9 g, 0.045 mol) with a solution of dimethyl sulfate (10 ml) in methanol (500 ml) for 5 minutes at 25° C, yield 2.74 g (0.0136 mol, 30%) after recrystallization. The structure of this compound was established by: $\lambda_{max}$ 4.5, 7.4, 7.6, 7.9, 8.6, 10.5, 12.0, 12.5, and 14.8 μm; $\lambda_{max}$ (CH$_3$CN) 337 nm (ε6363); $^1$H NMR (CDCl$_3$ $_{-Me_4Si}$) δ 2.60 (s) and 2.75 (s) ppm (SCH$_3$); $^{13}$C NMR (CD$_3$CN- Me$_4$Si) 167.4, 137.5, 133.4, 110.96, 17.4 and 14.31 ppm.

Anal. Calcd for C$_6$H$_6$N$_2$S$_3$: C, 35.62; H, 2.99; N, 13.85; Found: C, 35.78; H, 3.19; N, 13.65 35.40 3.14 13.54.

The acetonitrile filtrate from the preparation of the disodium salt above was evaporated and a solution of tetrapropylammonium bromide (10 g, 0.038 mol) in water (150 ml) was added with stirring to the residue. The resulting suspension was filtered, and the residue of crude 3-[(2-mercapto-1,2-dicyanovinyl)mercapto]-4-mercaptoisothiazole-5-carbonitrile bis(tetrapropylammonium) salt (5) was recrystallized from ethanol to give a first crop of 5.68 g of orange solid mp 182°–192° C. The structure of this salt was established by: $\lambda_{max}$(KBr) 4.53 (C≡N), 6.80, 6.98, 8.15, 8.68, 8.83, 10.15, 10.30, 10.60 and 11.88 μm.

Anal. Calcd. for $C_{32}H_{56}N_6S_4$: C, 58.85; H, 8.64; N, 12.87; S, 19.6; Found: C, 58.2 H, 8.79; N, 12.3; S, 18.7 12.3.

EXAMPLE 3

3,4-Dimercaptoisothiazole-5-carbonitrile Disodium Salt (3) (Tetracyano-1,4-dithiin Catalyst)

The procedure of Example 2 was repeated with 1,2-dimercaptomaleonitrile disodium salt (1) (186.0 g, 1.0 mol), sulfur (40.0 g, 1.25 g-atom), tetracyano-1,4dithiin (4) (21.6 g, 0.10 mol) and ethanol (2500 ml) with a 3.5-hour reflux time. This gave 102.5 g (0.47 mol, 83% conversion, 56% yield) of 3,4-dimercaptoisothiazole-5-carbonitrile disodium salt (3), mp 283° C dec, and 117.0 g (0.17 mol) of 3-[(2-mercapto-1,2-dicyanovinyl)mercapto]-4-mercaptoisothiazole-5-carbonitrile bis (tetrapropylammonium)salt (5). The 3,4-dimercaptoisothiazole-5-carbonitrile disodium salt had $\lambda_{max}$ 4.53, 7.60, 8.30, 8.90, 9.0, 10.5, 12.1 and 12.5 μm.

Anal. Calcd. for $C_4N_2S_3Na_2$: C, 22.02; N, 12.84; S, 44.08; Found: C, 21.71; N, 13.06; S, 28.0, 29.4.

Table I below lists Examples 4–6 in which the effects of varying the solvent and reaction time were studied in similar experiments to Examples 2 and 3.

Table I:

| | Preparation of 3,4-Dimercaptoisothiazole-5-carbonitrile Disodium Salt Under Various Conditions | | |
|---|---|---|---|
| Ex. | Reactants | Reflux Time | Yield |
| 4 | As in Example 3 | | 43% |
| 5 | As in Example 3 | 4h | 38% |
| 6 | As in Example 3 | 2h | 53% |
| Control-A | Salt 1 (9.3 g, 0.05 mol) Sulfur (2.0 g, 0.0625 g-atom) Dithiin 4 (1.1g, 0.005 mol) Diisopropylethylamine (0.2 ml) 1,2-Dimethoxyethane (100 ml) | 17h | Similar mixture to Example 1 |

EXAMPLE 7

3,4-Dimercaptoisothiazole-5-carbonitrile Disodium Salt (3)
(3-[(2-Mercapto-1,2-dicyanovinyl)mercapto]-4-mercaptoisothiazole-5-carbonitrile bis(tetrapropylammonium) Salt Catalyst)

The procedure of Example 3 was followed except that 3-[(2-mercapto-1,2-dicyanovinyl)mercapto]-4-mercaptoisothiazole-5-carbonitrile bis(tetrapropylammonium)salt (5) (65 g, 0.10 mol) was used in place of tetracyano-1,4-dithiin (4) as the catalyst. The yield was 22% with a 2-h reflux time and 43% with a 1.5-h reflux time.

EXAMPLE 8

[1,2,5,6]Tetrathiocino[3,4-c; 7,8-c′]diisothiazole-3,8-dicarbonitrile (6) from 3,4-Dimercaptoisothiazole-5-carbonitrile Disodium Salt (3) (Bromine method)

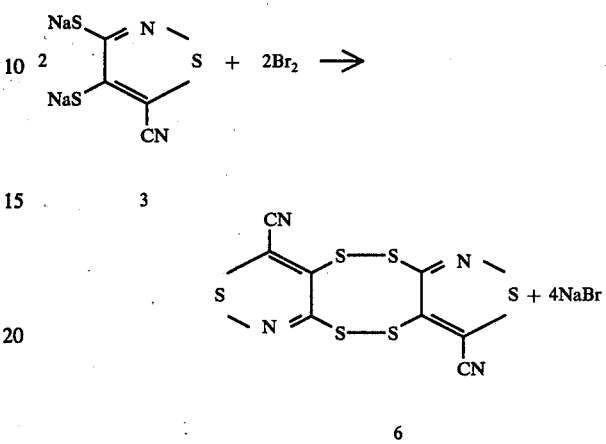

A suspension of 3,4-dimercaptoisothiazole-5-carbonitrile disodium salt (3) (10.9 g, 0.05 mol) in acetonitrile (100 ml) was cooled to 0° C and treated dropwise with bromine (11 ml, 34.1 g, 0.21 mol). The mixture was stirred at 0° C for 0.5 h and at room temperature for a further 1 h, filtered, and the solid was washed with acetonitrile and dried to give 7.05 g (0.02 mol, 100%) of product 6, mp 247°–249° C. Material from a similar experiment had mp 252°–254° C characterized by IR $\lambda_{max}$(KBr) 4.51, 7.85, 8.82, 10.54, 12.15, 12.54 and 14.36 μm.

Anal. Calcd for $C_8N_4S_6$: C, 27.89; N, 16.26; S, 55.84; Found: C, 26.01; N, 15.28; S, 53.1. 26.21; 15.21.

EXAMPLE 9

[1,2,5,6]Tetrathiocino[3,4-c; 7,8-c′]diisothiazole-3,8-dicarbonitrile (6) from 3,4-Dimercaptoisothiazole-5-carbonitrile Disodium Salt (3)(Hydrogen Peroxide Method)

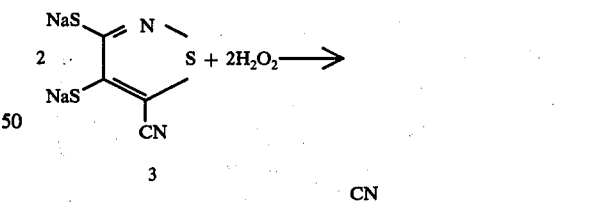

A solution of 3,4-dimercaptoisothiazole-5-carbonitrile disodium salt (3) (10.8 g, 0.05 mol) in water (250 ml) was cooled to 0°–5° C and treated dropwise simultaneously with 30% hydrogen peroxide (10 ml, 0.116 mol) and 6N sulfuric acid so that the solution was maintained at about pH 9.75 (monitored by pH meter). During the addition, the reaction temperature was maintained below 30° C, and then the mixture was stirred at room temperature overnight and filtered. The solid residue was washed successively with acetonitrile and dichloromethane and dried to give 2.31 g (0.007 mol, 27%) of product 6 which was identified as the compound of Example 8 by infrared spectrum.

In Table II, Examples 10–12 illustrate variations of the above procedure.

Additional analytical data were obtained on another sample of the product.

C. Ultraviolet maxima UV(CH$_3$CN): $\lambda_{max}$ 338 nm($\epsilon$ 10,900), 278 (14,950), 218 (25,000)

D. Carbon - 13 nuclear magnetic resonance spectrum ($^{13}$C-nmr) was run in dimethyl sulfoxide —d$_6$(DMSO-d$_6$) at 100° C. Chromium acetylacetonate (0.01 g) was added to lock signals. The analysis showed four none-

Table II:

| Ex. | Reactants | | Hydrogen Peroxide Method | | | |
|---|---|---|---|---|---|---|
| | | | pH | Temperature | Reaction Time[a] | Yield |
| 10 | Salt 3 | 21.6 g (0.1 mol) | 9.5 | 5° C | 1 h | 8.35 g (0.024 mol, 48%) |
| | Water | 500 ml | added simul- | | | |
| | 30% Hydrogen Peroxide | 30 ml (0.35 mol) | taneously | | | |
| | 6N Sulfuric Acid | 23 ml (0.07 mol) | | | | |
| 11 | Salt 3 | 21.6 g (0.1 mol) | 6–7 | 0° C | 0.5 h | 10.41 g (0.03 mol, 60%) |
| | Water | 500 ml | | | | |
| | 30% Hydrogen peroxide | 8.5 ml (0.1 mol | premixed | | | |
| | 6N Sulfuric Acid | 33 ml (0.1 mol) | | | | |
| 12 | Salt 3 | 108 g (0.5 mol) | 6–7 | 25° C | 2 h | 44.0 g (0.128 mol, 51%) |
| | Water | 2500 ml | | | | |
| | 30% Hydrogen peroxide | 68 ml (0.79 mol) | premixed | | | |
| | 6N Sulfuric acid | 264 ml (0.79 mol) | | | | |

[a]Following the addition period

CONTROL EXAMPLE B 1,4-Dithiino[2,3-c; 6,5-c']diisothiazole-3,7-dicarbonitrile (7) (From Tetracyano-1,4-dithiin)

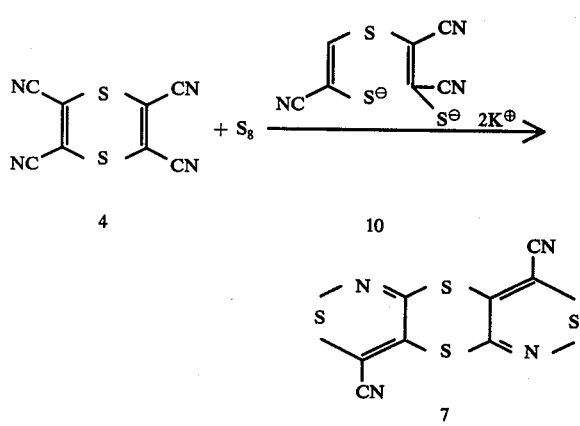

Tetracyano-1,4-dithiin (4) (4.32 g, 20 meq) was added to a stirred solution of sulfur (2.69 g, 84 meq) and the dipotassium salt of bis(2-mercapto-1,2-dicyanovinyl)sulfide (10) catalyst (0.6 g, 2 meq) in 200 ml of 1,2-dimethoxymethane. The yellow-green solution quickly turned dark orange, and the reaction mixture was heated under reflux (83°–84° C) overnight. The solution was cooled and the solvent removed at reduced pressure. The residue was extracted with water and filtered to leave an 87% yield of crude solid product. This crude product was sublimed at 235° C ($\approx$0.1 mm, oil pump) and it was recrystallized twice from toluene to give pure 1,4-dithiino[2,3-c; 6,5-c']diisothiazole-3,7-dicarbonitrile (7) as a pale yellow solid, mp 286°–289° C.

Anal. calcd for C$_8$N$_4$S$_4$: c, 34.3; N, 20.0; S, 45.7; Found: c, 34.6; N, 20.0; S, 45.4. The following spectral and analytical data confirm the structure of formula 7:

A. Infrared maxima IR (KBr): 4.50 (s, CN), 6.78 (s), 7.48, 7.58, 7.78 (s), 8.68, 10.43 (s), 11.85 (s), 12.30 (s), 14.58 and 14.98 $\mu$m B. Dipole moment measured at 25° C in dioxane, $\mu$ = 3.82D; 3.59D.

quivalent carbon atoms at 153.2, 133.0, 127.2 and 108.3 (CN) ppm from tetramethylsilane reference.

E. High resolution mass spectral analysis showed a measured m/e of 279.8988 in agreement with the molecular formula C$_8$N$_4$S$_4$ (Calcd. for C$_8$N$_4$S$_4$: m/e 279.9006).

F. The crystal and molecular structures of 3,7-dicyano-1,4-dithiino[2,3-c; 6,5-c']diisothiazole (7) were determined from three-dimensional X-ray data collected by counter methods such as on a Picker diffractometer. Tthe molecular conformation is unambiguously established as trans as shown in formula I. The molecular point symmetry is C$_2$(2) with the twofold axis normal to the 1,4-sulfur atoms. The molecule is folded along the 1,4-S . . . S direction and planar to within 0.04 A on both sides of the fold. The angle of fold is 144.9° as measured by the angle between the two 5-membered isothiazole rings. The folded molecules are stacked along the b axis with 3.808 Å between sulfur atoms on adjacent molecules; the perpendicular distance between isothiazole rings is 3.614 Å.

Crystals are monoclinic, space group C2/c, with $a$ = 12.836±0.006, $b$ = 3.808±0.002, $c$ = 21.060±0.008Å, and $\beta$ = 104.91±0.03°. The density for four molecules per cell is 1.87 g cm$^{-3}$. These data establish that the molecular structure of 3,7-dicyano-1,4-dithiino[2,3-c; 6,5-c']diisothiazole is trans as shown in 7.

The dipotassium salt of bis(2-mercapto-1,2-dicyanovinyl)sulfide (10) employed as a catalyst was prepared by the following procedure. Tetracyano-1,4-dithiin (4) (10.8 g, 0.05 mole) in 200 ml of acetone was added over one-half hour to 16.0 g (0.1 mole) of potassium ethyl xanthate in 500 ml of acetone. After one-half hour of additional stirring, the solvents were removed in vacuo, and the residue was extracted several times with 50-ml portions of low-boiling petroleum ether under reflux. The insoluble residue (19 g) was dissolved in 300 ml of acetone, filtered and 1 l. of chloroform was added to the filtrate. A total of 11 g (65%) of the dipotassium salt of bis(2-mercapto-1,2-dicyanovinyl)sulfide (10) was obtained as a yellow solid which melted with decomposition at 280°–285° C. The infrared spectrum showed characteristic bands at 4.53 (C≡N) and 6.76 $\mu$m (C=C) and the ultraviolet spectrum (EtOH) showed $\lambda_{max}$ 380 nm ($\epsilon$ 18,400) and 218 (16,950).

Anal. Calcd. for $C_8N_4S_3K_2$: C, 29.42; H, 0.00; N, 17.16; S, 29.46; Found: C, 28.70; H, 0.40; N, 17.31; S, 29.51.

EXAMPLE 13

1,4-Dithiino[2,3-c; 6,5-c']diisothiazole-3,7-dicarbonitrile(7) from [1,2,5,6]Tetrathiocino[3,4-c; 7,8-c']diisothiazole-3,8-dicarbonitrile (6) (Thermal Method)

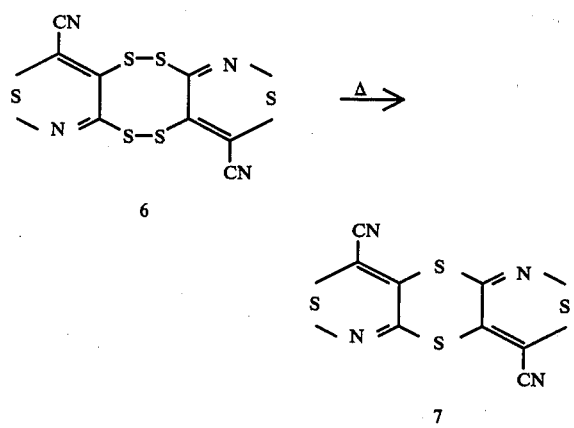

A suspension of [1,2,5,6]tetrathiocino[3,4-c; 7,8-c']diisothiazole-3,8-dicarbonitrile (6) (0.5 g, 1.4 mmol) in trichlorobenzene (10 ml) was heated at reflux overnight, cooled and filtered. The residue of 1,4-dithiino[2,3-c; 6,5-c']diisothiazole-3,7-dicarbonitrile (7) (0.28 g, 1.0 mmole, 71%) was identified by comparison of its infrared spectrum with that of an authentic sample prepared by the procedure of Control Example B.

EXAMPLE 14

1,4-Dithiino[2,3-c; 6,5-c']diisothiazole-3,7-dicarbonitrile (7) from [1,2,5,6]Tetrathiocino[3,4-c; 7,8-c']diisothiazole-3,8-dicarbonitrile (6) (Catalytic Method)

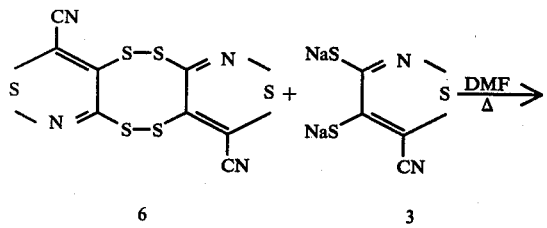

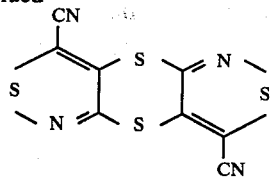

A mixture of [1,2,5,6]tetrathiocino[3,4-c; 7,8-c']diisothiazole-3,8-dicarbonitrile (6) (3.44 g, 10 mmol), 3,4-dimercaptoisothiazole-5-carbonitrile disodium salt (0.50 g, 2.3 mmol) and N,N-dimethylformamide (50 ml) was heated at 100° C for 2h. The mixture was cooled to 0° C and filtered; the filtrate was poured over ice, and the crude solid product was isolated by filtration. This material was recrystallized from toluene, yield 1.66 g (5.92 mmol, 59%) of 1,4-dithiino[2,3-c; 6,5-c']diisothiazole-3,7-dicarbonitrile (7), identified by comparison of its infrared spectrum with that of an authentic sample of Control Example B.

3,4-Dimercaptoisothiazole-5-carbonitrile disodium salt (3) and [1,2,5,6]tetrathiocino[3,4-c; 7,8-c']diisothiazole-3,8-dicarbonitrile (6) are useful curing agents for natural rubber, as demonstrated by Example A.

EXAMPLE A

Rubber compounding was carried out in a rubber mill by mixing the ingredients shown below in the order given at 70° C; the compound stock was then cured in a mold at 140° C for 40 min. All parts given are by weight, and the results are summarized in Table III below.

Table III:

| | Rubber Curing Experiments | |
|---|---|---|
| Sample | Composition | Results |
| 1) Control | 20 parts natural rubber<br>1.2 parts zinc oxide<br>0.1 part stearicacid<br>0.1 part mercaptobenzo-isothiazole | Brittle gummy material which breaks on elongation (no elasticity or tensile strength) |
| 2) | Control plus<br>0.88 part 3,4-dimercapto-isothiazole-5-carbonitrile disodium salt (3) | Cured rubber of high elasticity and good tensile strength |
| 3 | Control plus<br>0.88 part [1,2,5,6]tetra-thiocino[3,4-c; 7,8-c']-diisothiazole-3,8-dicarbon-trile (6) | Cured rubber of high elasticity and excellent tensile strength |

What is claimed is:

1. A process for preparing a disalt of the 3,4-dimercaptoisothiazole-5-carbonitrile comprising the step of contacting a 1,2-dimercaptomaleonitrile salt of the formula

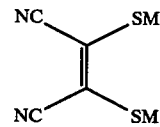

where M is an alkali metal or bis[tetra (lower alkyl ammonium)], with sulfur in a solvent selected from the group consisting of alkanols, aqueous alkanols, and mixtures of alkanols with a dipolar aprotic solvent at a temperature of at least 50° C.

2. The process of claim 1 wherein the contacting is conducted in the presence of a catalytic amount of tetracyano-1,4-diithin or a compound of the formula

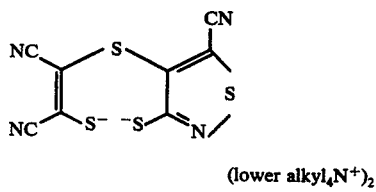

(lower alkyl$_4$N$^+$)$_2$

3. The process of claim 2 wherein the temperature is in the range of about 50°–150° C.
4. The process of claim 3 wherein each M is Na.
5. The process of claim 4 wherein the solvent is at least one alkanol of 1–6 carbon atoms.
6. The process of claim 5 wherein the temperature is in the range of about 60°–100° C.
7. The process of claim 6 wherein the alkanol solvent is ethanol.
8. The process of claim 5 wherein about 1–1.2 g-atoms of sulfur are used per mole of the disodium salt of 1,2-dimercaptomaleonitrile.

* * * * *